US008440454B2

(12) United States Patent
Shin et al.

(10) Patent No.: US 8,440,454 B2

(45) **Date of Patent: *May 14, 2013**

(54) PASTING EDGE HEATER

(75) Inventors: Hon Siu Shin, Singapore (SG); Hock Lai Khoo, Singapore (SG)

(73) Assignee: Applied Biosystems, LLC, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/095,274

(22) Filed: Apr. 27, 2011

(65) Prior Publication Data

US 2011/0200501 A1 Aug. 18, 2011

Related U.S. Application Data

(63) Continuation of application No. 12/697,146, filed on Jan. 29, 2010, now Pat. No. 7,935,524, which is a continuation of application No. 10/848,593, filed on May 17, 2004, now Pat. No. 7,659,109.

(51) Int. Cl.

| | |
|---|---|
| ***C12M 1/00*** | (2006.01) |
| ***C12M 1/34*** | (2006.01) |
| ***C12M 3/00*** | (2006.01) |
| ***C12M 1/22*** | (2006.01) |

(52) U.S. Cl.

USPC .................. 435/288.4; 435/283.1; 435/287.2; 435/288.3; 435/303.1; 435/305.2

(58) Field of Classification Search ..... 435/283.1–309.4
See application file for complete search history.

(56) References Cited

U.S. PATENT DOCUMENTS

| | | | | |
|---|---|---|---|---|
| 4,345,837 | A * | 8/1982 | Kallet | 356/317 |
| 5,475,610 | A * | 12/1995 | Atwood et al. | 700/269 |
| 6,334,980 | B1 | 1/2002 | Hayes et al. | |
| 6,337,435 | B1 * | 1/2002 | Chu et al. | 136/242 |
| 6,703,236 | B2 | 3/2004 | Atwood | |
| 6,730,883 | B2 * | 5/2004 | Brown et al. | 219/428 |
| 7,133,726 | B1 | 11/2006 | Atwood et al. | |
| 7,659,109 | B2 * | 2/2010 | Shin et al. | 435/303.1 |
| 7,935,524 | B2 | 5/2011 | Shin et al. | |
| 2002/0030044 | A1 | 3/2002 | Brown | |
| 2003/0106682 | A1 * | 6/2003 | Reid et al. | 165/206 |
| 2004/0241048 | A1 | 12/2004 | Shin et al. | |
| 2005/0184042 | A1 * | 8/2005 | Brown et al. | 219/428 |
| 2010/0129876 | A1 | 5/2010 | Shin et al. | |

FOREIGN PATENT DOCUMENTS

WO WO-98/43740 10/1998

OTHER PUBLICATIONS

U.S. Appl. No. 10/848,593, Notice of Allowance mailed Sep. 25, 2009.
10013122.6, Extended European Search Report mailed Mar. 15, 2011.
U.S. Appl. No. 12/697,146, Notice of Allowance mailed Dec. 23, 2010.
U.S. Appl. No. 12/697,146, Notice of Allowance mailed Sep. 27, 2010.
U.S. Appl. No. 12/697,146, Office Action mailed May 25, 2010.

(Continued)

*Primary Examiner* — Nathan Bowers
*Assistant Examiner* — Lydia Edwards

(57) ABSTRACT

An apparatus and method for thermal cycling including a pasting edge heater. The pasting edge heater can provide substantial temperature uniformity throughout the retaining elements during thermal cycling by a thermoelectric module.

20 Claims, 6 Drawing Sheets

OTHER PUBLICATIONS

International Search Report for Application No. PCT/US2005/017317 mailed on Oct. 19, 2005, along with Written Opinion of the International Searching Authority.

* cited by examiner

PASTING EDGE HEATER

CROSS-REFERENCE TO RELATED APPLICATION

This application is a continuation of application Ser. No. 12/697,146 filed Jan. 29, 2010, which is a continuation of application Ser. No. 10/848,593 filed May 17, 2004, all of which are incorporated herein by reference.

FIELD

The present teachings relate to thermal cycling of biological samples. Improvement in thermal cycling can be provided by a pasting edge heater.

INTRODUCTION

In the biological field, thermal cycling can be utilized to provide heating and cooling of reactants in a reaction vessel. Examples of reactions of biological samples include polymerase chain reaction (PCR) and other reactions such as ligase chain reaction, antibody binding reaction, oligonucleotide ligations assay, and hybridization assay. In PCR, biological samples can be thermally cycled through a temperature-time protocol that includes melting DNA into single strands, annealing primers to the single strands, and extending those primers to make new copies of double-stranded DNA. During thermal cycling, it is desirable to maintain thermal uniformity throughout a set of retaining elements so that different sample wells can be heated and cooled uniformly to obtain uniform sample yields. Uniform yields can provide quantification between samples wells. According to the present teachings, a pasting edge heater can provide thermal uniformity to the retaining elements of a thermal cycling device.

SUMMARY

According to various embodiments, an apparatus for thermally cycling biological samples can include a plurality of retaining elements for receiving a plurality of sample wells containing the biological samples, wherein the retaining elements comprise a bottom surface and an edge surface, a thermoelectric module coupled to the bottom surface of the retaining elements, and an edge heater coupled to the edge surface, wherein an adhesive couples edge heater to the edge surface.

According to various embodiments, a method for thermal cycling biological samples can include providing a plurality of retaining elements adapted to releasably couple to a plurality of wells containing the biological samples, wherein the retaining elements comprise an edge surface with an edge heater coupled to the edge surface, heating the retaining elements with the edge heater, cooling the retaining elements.

According to various embodiments, a device for thermal cycling of biological samples can include means for containing the biological samples, means for cooling the biological samples, and means for heating an edge surface of the means for containing.

According to various embodiments, a system for thermal cycling of biological samples can include a plurality of retaining elements adapted to receive a plurality of wells containing the biological samples, wherein the retaining elements comprise a bottom surface and an edge surface, a thermoelectric module coupled to the bottom surface of the retaining elements, an edge heater coupled to the edge surface, an excitation light source adapted to induce fluorescent light to be emitted by the biological samples during thermal cycling, and a detector adapted to collecting the fluorescent light emitted.

It is to be understood that both the foregoing general description and the following description of various embodiments are exemplary and explanatory only and are not restrictive.

BRIEF DESCRIPTION OF THE DRAWINGS

The accompanying drawings, which are incorporated in and constitute a part of this specification, illustrate various embodiments. In the drawings.

DESCRIPTION OF VARIOUS EMBODIMENTS

Figure 1A:
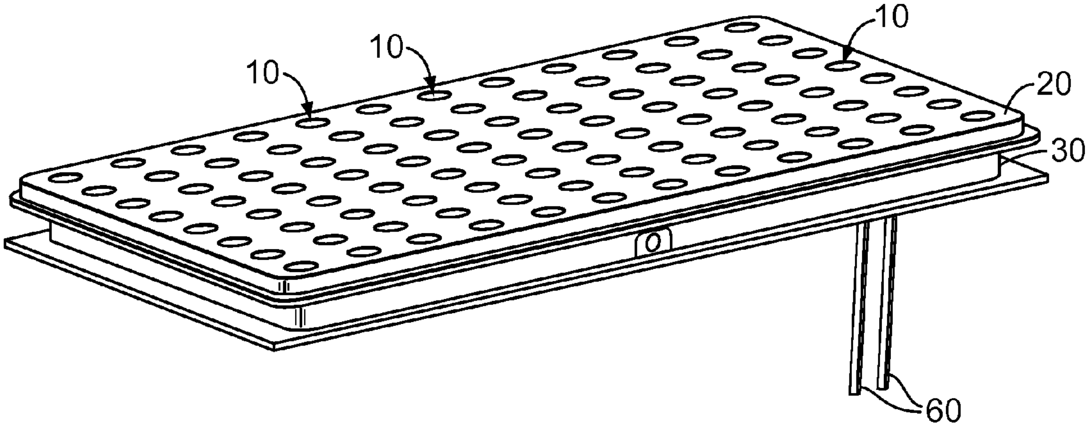
FIGS. 1A-1B illustrate a perspective view of retaining elements with different types of edge heaters according to various embodiments.
Figure 1B:
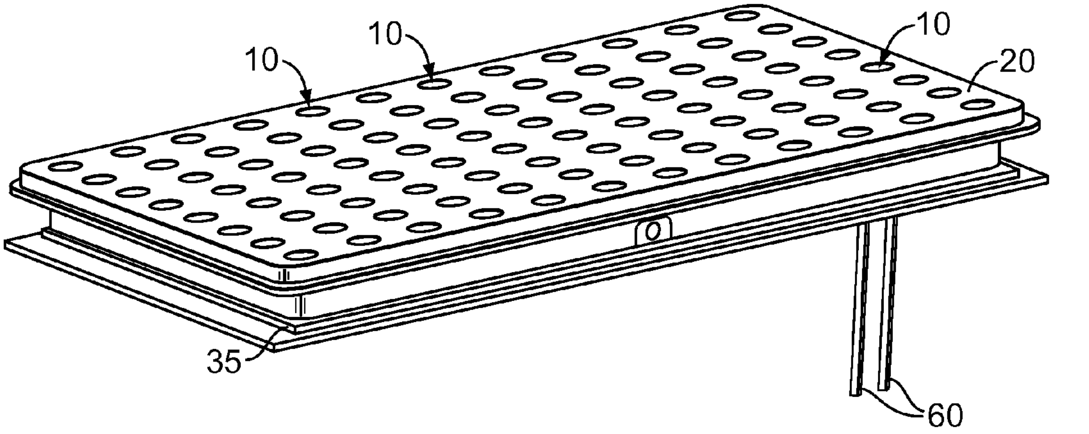
Figure 2A:
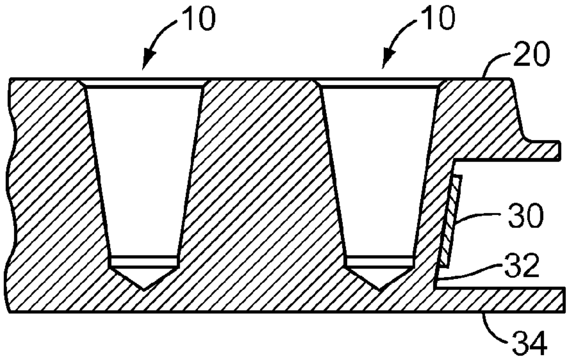
FIGS. 2A-2B illustrate a cross-sectional view of the retaining elements in FIGS. 1A-1B showing the different types of edge heaters according to various embodiments.
Figure 2B:
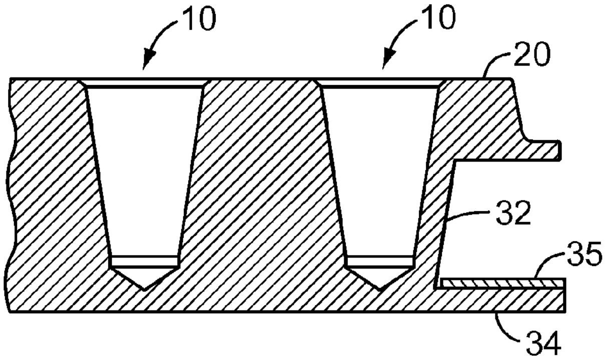

In this application, the use of the singular includes the plural unless specifically stated otherwise. In this application, the use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise. Wherever possible, the same reference numbers will be used throughout the drawings to refer to the same or like parts.

The section headings used herein are for organizational purposes only, and are not to be construed as limiting the subject matter described. All documents cited in this application, including, but not limited to patents, patent applications, articles, books, and treatises, are expressly incorporated by reference in their entirety for any purpose.

The term "retaining element" or "retaining elements" as used herein refer to the component into which sample wells are positioned to be thermally cycled. The retaining element provides containment for wells and thermal mass for heating and cooling during the thermal cycling. The retaining element can provide a collection of several cavities in a variety of forms such as a strip of cavities or an array of cavities. The retaining element includes bottom surface oriented in a direction such that it contacts the thermoelectric module and an inner surface oriented in a direction such that it couples with the sample wells. The retaining elements can have varying physical dimensions.

The term "thermal cycling" or grammatical variations of such as used herein refer to heating, cooling, temperature ramping up, and/or temperature ramping down. Thermal cycling during temperature ramping up, when heating the thermal block assembly above ambient (20° C.), can comprise resistive heating of the thermal block assembly and/or pumping heat into the thermal block assembly by the thermoelectric module against diffusion of heat away from the thermal block assembly. Thermal cycling during temperature ramping down, when cooling the thermal block assembly above ambient (20° C.), can comprise pumping heat out of the thermal block assembly by the thermoelectric module and diffusion of heat away from the thermal block assembly against resistive heating.

The term "wells" as used herein refers to any structure that provides containment to the sample. The wells can be open or transparent to provide entry to excitation light and exit to fluorescent light. The transparency can be provided glass, plastic, fused silica, etc. The well can take any shape including a tube, a vial, a cuvette, a tray, a multi-well tray, a microcard, a microslide, a capillary, an etched channel plate, a molded channel plate, an embossed channel plate, etc. The wells can be part of a combination of multiple wells grouped into a row, an array, an assembly, etc. Multi-well arrays can include 12, 24, 36, 48, 96, 192, 384, or more, sample wells. The wells can be shaped to a multi-well tray under the SBS microtiter format.

The term "heater" as used herein refers to devices that provide heat. Heaters can include, but are not limited to, resistive heaters.

The term "sample" as used herein includes any reagents, solids, liquids, and/or gases. Exemplary samples may comprise anything capable of being thermally cycled.

The term "thermoelectric module" as used herein refers to Peltier devices, also known as thermoelectric coolers (TEC), that are solid-state devices that function as heat pumps. In various embodiments, the thermoelectric module can comprise two ceramic plates or two layers of Kapton thin film with a bismuth telluride composition between the two plates or two layers. In various embodiments, when an electric current can be applied, heat is moved from one side of the device to the other, where it can be removed with a heat sink and/or a thermal diffusivity plate. In various embodiments, the "cold" side can be used to pump heat out of a thermal block assembly. In various embodiments, if the current is reversed, the device can be used to pump heat into the thermal block assembly. In various embodiments, thermoelectric modules can be stacked to achieve an increase in the cooling and heating effects of heat pumping. Thermoelectric modules are known in the art and manufactured by several companies, including, but not limited to, Tellurex Corporation (Traverse City, Mich.), Marlow Industries (Dallas, Tex.), Melcor (Trenton, N.J.), and Ferrotec America Corporation (Nashua, N.H.).

The term "excitation light source" as used herein refers to a source of irradiance that can provide excitation that results in fluorescent emission. Light sources can include, but are not limited to, white light, halogen lamp, lasers, solid state laser, laser diode, micro-wire laser, diode solid state lasers (DSSL), vertical-cavity surface-emitting lasers (VCSEL), LEDs, phosphor coated LEDs, organic LEDs (OLED), thin-film electroluminescent devices (TFELD), phosphorescent OLEDs (PHOLED), inorganic-organic LEDs, LEDs using quantum dot technology, LED arrays, filament lamps, arc lamps, gas lamps, and fluorescent tubes. Light sources can have high irradiance, such as lasers, or low irradiance, such as LEDs. The different types of LEDs mentioned above can have a medium to high irradiance.

The term "detector" as used herein refers to any component, portion thereof, or system of components that can detect light including a charged coupled device (CCD), back-side thin-cooled CCD, front-side illuminated CCD, a CCD array, a photodiode, a photodiode array, a photo-multiplier tube (PMT), a PMT array, complimentary metal-oxide semiconductor (CMOS) sensors, CMOS arrays, a charge-injection device (CID), CID arrays, etc. The detector can be adapted to relay information to a data collection device for storage, correlation, and/or manipulation of data, for example, a computer, or other signal processing system.

Figure 3:
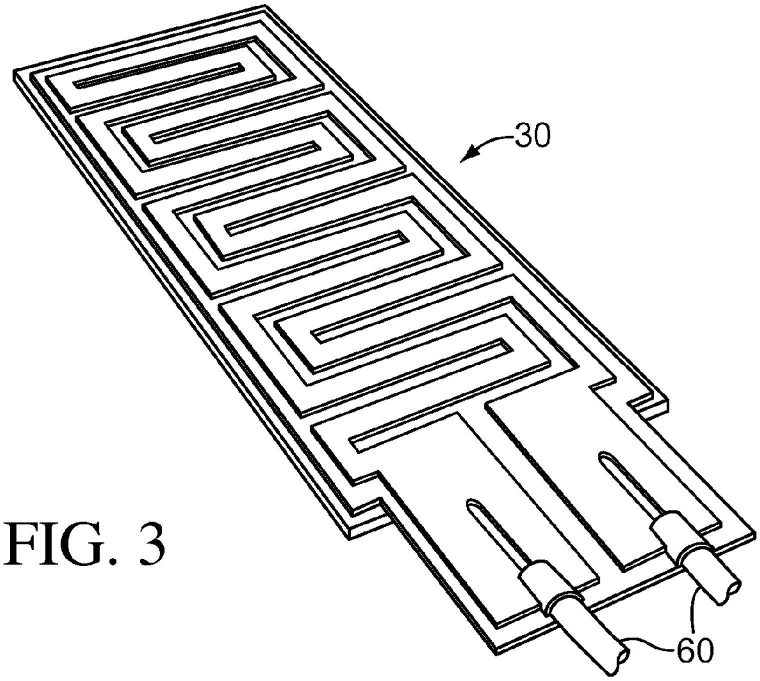
FIG. 3 illustrates a perspective view of an edge heater according to various embodiments.

According to various embodiments, as illustrated in FIGS. 1A-1B and 2A-2B, edge heaters include pasting heaters 30 and floating heaters 35. Pasting heater 30 couples to edge surface 32 of retaining elements 20. Floating heater 35 couples to the top side of bottom surface 34 of retaining elements 20. Coupling pasting heater 30 to the edge surface 32 provides closer proximity to the cavity 10 where sample wells can be releasably positioned. According to various embodiments, as illustrated in FIGS. 1A and 3, pasting heater 30 can be powered by electric leads 60.

Figure 4:
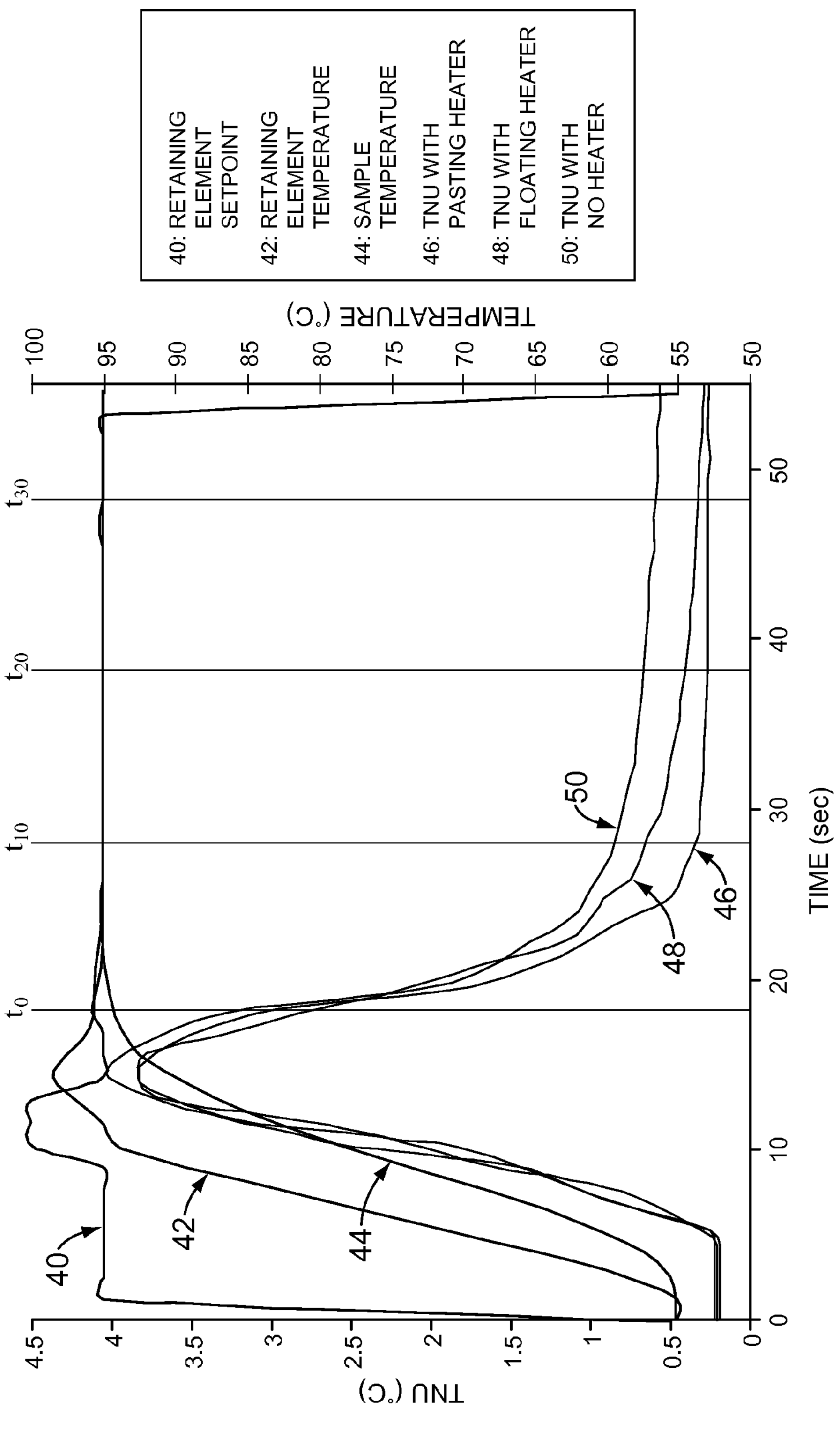
FIG. 4 illustrates a graph showing temperature nonuniformity ("TNU") and temperature versus time for thermal cycling with edge heaters according to various embodiments.

According to various embodiments, as illustrated in FIG. 4, coupling a pasting heater to the retaining elements reduces TNU as compared to coupling a floating heater or providing no edge heater at all. The graph in FIG. 4 shows TNU in degrees centigrade on the left axis, temperature in degrees centigrade on the right axis and time in seconds on the bottom axis. Line 40 represents the retaining element set point temperature showing an ramp up to 95 degrees centigrade with a step change to 100 degrees centigrade between 10 and 15 seconds from the start of the of the cycling. Line 42 represents the actual retaining element temperature of the wells measured in degrees centigrade and line 44 represents the sample temperature in degrees centigrade. These values reach with 95 percent of 95 degrees centigrade at time $t_0$. At that point it is desirable that the TNU be minimized in the shortest amount of time. This is observed by monitoring the TNU at times $t_{10}$, $t_{20}$, and $t_{30}$ which represent 10, 20, and 30 seconds after $t_0$. At $t_{10}$, line 46 that represents the embodiment with a pasting heater has the lowest TNU, line 48 that represents the embodiment with a floating heater has a higher TNU, and line 50 that represents the embodiment with no edge heater has the highest TNU. This behavior persists through $t_{20}$ and $t_{30}$ with the exception that line 48 approaches line 46, indicating that the floating heater can reach the TNU of the pasting heater, but requires a significantly longer period of time.

Figure 5:
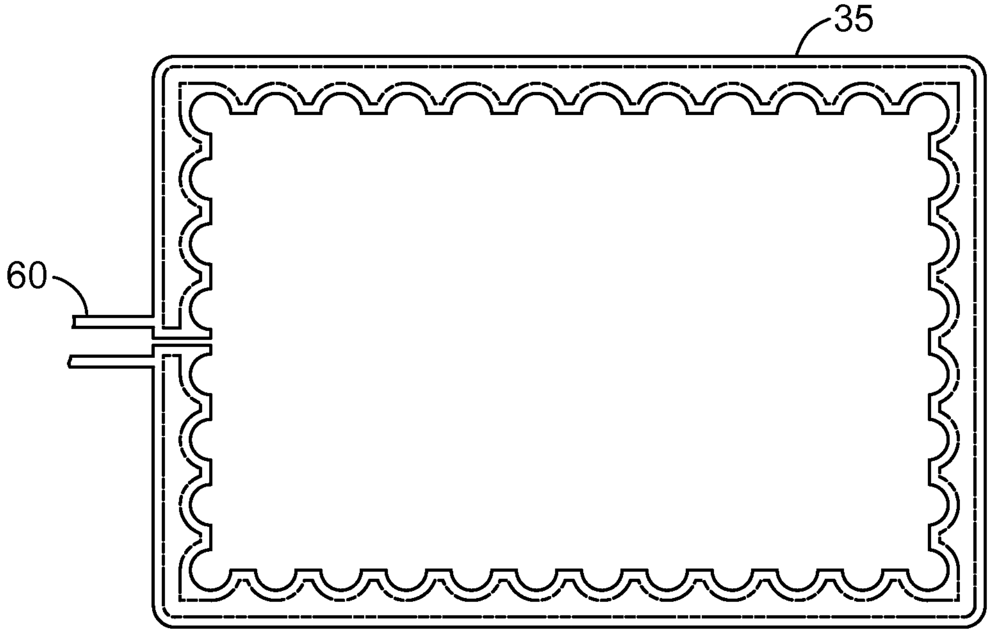
FIG. 5 illustrates a top view of an edge heater according to various embodiments.
Figure 6:
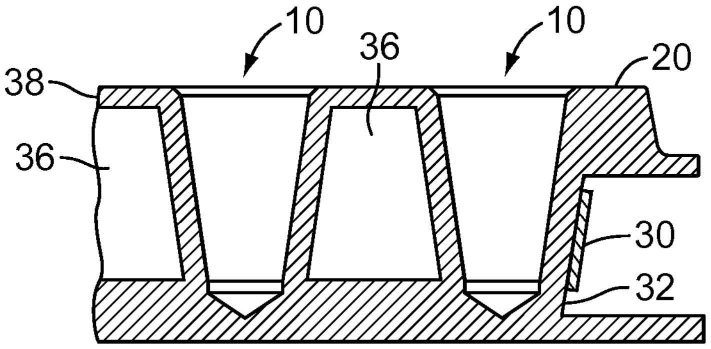
FIG. 6 illustrates a cross-sectional view of retaining elements with edge heaters according to various embodiments.

According to various embodiments, as illustrated in FIG. 6, the retaining elements 20 can be separated by voids 36 such that each cavity 10 is separated and connected to other cavities 10 by as little as two ribs. As shown, the two cavities can be connected by ribs 38 only in the plane of cross-section and not on the perpendicular plane, or the two cavities can be connected by ribs 38 in both planes. Ribs 38 reduce the thermal mass of the retaining elements 20. As shown, FIG. 6 illustrates a flat edge surface 32. According to various embodiments, the edge surface can be curved such as the kind that would require a floating heater 35 as illustrated in FIG. 5. A pasting edge heater can 30 can be coupled to the curved surface and take a similar cross-section as the floating heater illustrated in FIG. 5.

Figure 7:
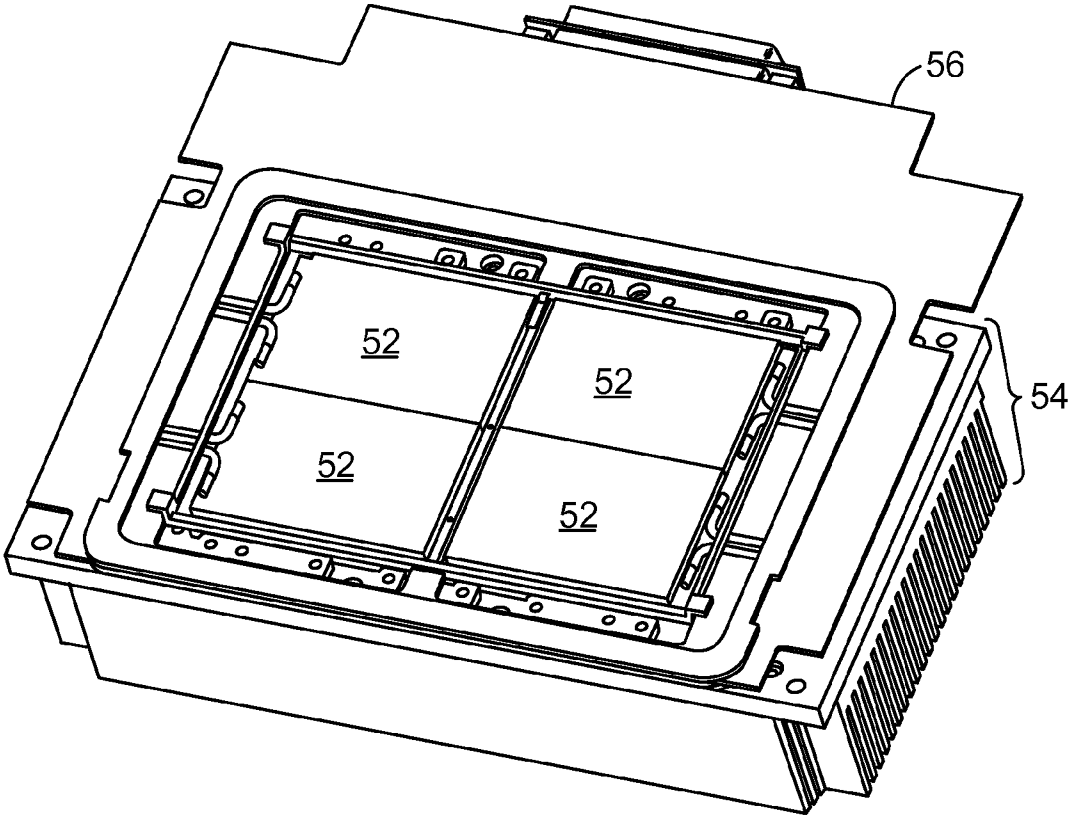
FIG. 7 illustrates a perspective view of a system for thermal cycling according to various embodiments without the retaining elements to show the thermoelectric modules.
Figure 8:
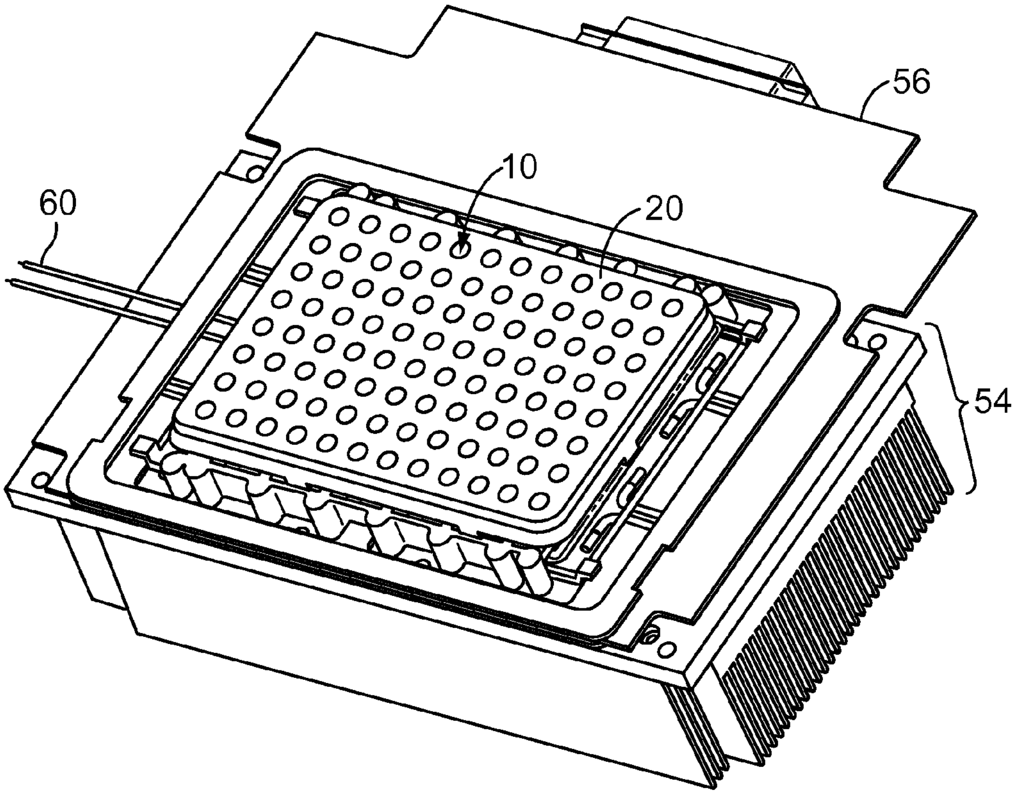
FIG. 8 illustrates a perspective view of the system in FIG. 7 with the retaining elements positioned on top of the thermoelectric modules.

According to various embodiments, as illustrated in FIGS. 7-8, a system for thermal cycling can include thermoelectric modules 52, heat sink 54, and control circuit board 56. FIG. 8 illustrates the retaining elements 20 positioned on top of the thermoelectric modules 52 such that leads 50 extend to the side of the retaining elements 20.

According to various embodiments, there are several examples of pasting heaters commercially available. For example, Thermafoil™ Heater (Minco Products, Inc., Minneapolis, Minn.), HEATFLEX Kapton™ Heater (Heatron, Inc., Leavenworth, Kans.), Flexible Heaters (Watlow Electric Manufacturing Company, St. Louis, Mo.), and Flexible Heaters (Ogden Manufacturing Company, Arlington Heights, Ill.).

According to various embodiments, the pasting heaters can be vulcanized silicone rubber heaters, for example Rubber Heater Assemblies (Minco Products, Inc.), SL-B Flexible Silicone Rubber Heaters (Chromalox, Inc., Pittsburgh, Pa.), Silicone Rubber Heaters (TransLogic, Inc., Huntington Beach, Calif.), Silicone Rubber Heaters (National Plastic Heater Sensor & Control Co., Scarborough, Ontario, Canada).

According to various embodiments, the pasting heater can be coupled to the edge surface with a variety of pressure-sensitive adhesive films. It is desirable to provide uniform thickness and lack of bubbles. Uniform thickness provides uniform contact and uniform heating. Bubbles under the pasting heater can cause localized overheating and possible heater burnout. Typically, pressure-sensitive adhesives cure at specified temperature ranges. Examples of pressure-sensitive adhesive films include Minco #10, Minco #12, Minco #19, Minco #17, and Ablefilm 550k (AbleStik Laboratories, Rancho Dominguez, Calif.).

According to various embodiments, the pasting heater can be coupled to the edge surface with liquid adhesives. Liquid adhesives are better suited for curved surfaces than pressure-sensitive adhesives. Liquid adhesives can include 1-part pastes, 2-part pastes, RTV, epoxies, etc. Bubbles can substantially avoided by special techniques such as drawing vacuum on the adhesive after mixing, or perforating heaters to permit the bubbles to escape. Examples of liquid adhesives include Minco #6, GE #566 (GE Silicones, Wilton, Conn.), Minco #15, Crest 3135 A/B (Lord Chemical, Cary, N.C.).

According to various embodiments, the pasting heater can be coupled to the edge surface by tape or shrink bands. Shrink bands can be constructed of Mylar or Kapton. Instead of an intermediate adhesive layer, the adhesive layer is moved to the top of the pasting heater. Examples of shrink bands and stretch tape include Minco BM3, Minco BK4, and Minco #20. According to various embodiments, the pasting heater can be laminated onto the edge surface, for example by films.

According to various embodiments, pasting edge heaters can be mechanically attached to the heating surface. For example, a pasting heater with eyelets have be attached with a lacing cord, Velcro hooks and loops, metallic fasteners with springs, and independent fasteners with straps.

For the purposes of this specification and appended claims, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "less than 10" includes any and all subranges between (and including) the minimum value of zero and the maximum value of 10, that is, any and all subranges having a minimum value of equal to or greater than zero and a maximum value of equal to or less than 10, e.g., 1 to 5.

It is noted that, as used in this specification and the appended claims, the singular forms "a," "an," and "the," include plural referents unless expressly and unequivocally limited to one referent. Thus, for example, reference to "a thermoelectric module" includes two or more thermoelectric modules.

It will be apparent to those skilled in the art that various modifications and variations can be made to various embodiments described herein without departing from the spirit or scope of the present teachings. Thus, it is intended that the various embodiments described herein cover other modifications and variations within the scope of the appended claims and their equivalents.

What is claimed is:

1. An apparatus for thermal cycling samples, the apparatus comprising:

a sample retaining element comprising a first surface for receiving a sample containment structure, a second surface opposing the first surface, and a substantially flat edge surface, wherein the first surface provides a plurality of sample wells, and wherein the substantially flat edge surface is a third surface located between the first surface and the second surface, and wherein the sample containment structure provides containment for a plurality of samples; and an edge heater coupled to the substantially flat edge surface of the sample retaining element, said edge heater adapted to reduce the temperature non-uniformity (TNU) of the sample retaining element;

wherein the TNU of the sample retaining element is between about 0.25° C. to about 0.50° C. within between about 5 seconds to about 10 seconds of achieving a sample retaining element temperature of about 95° C.

2. The apparatus of claim 1, wherein at least one thermal electric module is in contact with the second surface of the sample retaining element.

3. The apparatus of claim 2, further comprising an excitation light source, an excitation light source adapted to induce light to be emitted by the plurality of samples during thermal cycling and a detector.

4. The apparatus of claim 3, further comprising an excitation light source a detector adapted to collecting the fluorescent light emitted by the plurality of samples.

5. The apparatus of claim 2, wherein the edge heater and the at least one thermoelectric module are separately controlled.

6. The apparatus of claim 1, wherein the sample retaining element provides a thermal mass for heating and cooling the sample containment structure during thermal cycling.

7. The apparatus of claim 1, wherein the edge heater is printed on the substantially flat edge surface of the sample retaining element.

8. The apparatus of claim 1, wherein the edge heater is a resistive heater.

9. The apparatus of claim 1, wherein the coupling comprises adhesive coupling.

10. The apparatus of claim 1, wherein the coupling comprises mechanical coupling.

11. An apparatus for thermal cycling samples, the apparatus comprising:

a sample retaining element comprising a first surface for receiving a sample containment structure, a second surface opposing the first surface, and a substantially flat edge surface, wherein the first surface provides a plurality of sample wells, and wherein the substantially flat edge surface is a third surface located between the first surface and the second surface, and wherein the sample retaining element provides a thermal mass for heating and cooling during thermal cycling; and an edge heater coupled to the substantially flat edge surface of the sample retaining element, said edge heater adapted to reduce the temperature nonuniformity (TNU) of the sample retaining element;

wherein the TNU of the sample retaining element is about 0.25° C. within between about 10 seconds to about 20 seconds of achieving a sample retaining element temperature of about 95° C.

12. The apparatus of claim 11, wherein at least one thermal electric module is in contact with the second surface of the sample retaining element.

13. The apparatus of claim 12, further comprising an excitation light source, an excitation light source adapted to induce light to be emitted by the plurality of samples during thermal cycling and a detector.

14. The apparatus of claim 13, further comprising an excitation light source a detector adapted to collecting the fluorescent light emitted by the plurality of samples.

15. The apparatus of claim 12, wherein the edge heater and the at least one thermoelectric module are separately controlled.

16. The apparatus of claim 11, wherein the edge heater is printed on the substantially flat edge surface of the sample retaining element.

17. The apparatus of claim 11, wherein the edge heater is a resistive heater.

18. The apparatus of claim 11, wherein the coupling comprises adhesive coupling.

19. The apparatus of claim 11, wherein the coupling comprises mechanical coupling.

20. An apparatus for thermal cycling samples, the apparatus comprising:

a sample retaining element comprising a first surface for receiving a sample containment structure, a second surface opposing the first surface, and a substantially flat surface, wherein the first surface provides a plurality of sample wells, and wherein the second surface is in thermal contact with at least one thermal electric module, and wherein the substantially flat surface is a third surface located between the first surface and the second surface, and wherein the sample retaining element provides a thermal mass for heating and cooling during thermal cycling; and a heater coupled to the substantially flat surface of the sample retaining element, and said heater adapted to reduce the temperature nonuniformity (TNU) of the sample retaining element.

* * * * *